US007993277B1

(12) United States Patent
Link

(10) Patent No.: US 7,993,277 B1
(45) Date of Patent: Aug. 9, 2011

(54) COMMOTIO CORDIS TESTING

(76) Inventor: Mark S. Link, Newton, MA (US)

( * ) Notice: Subject to any disclaimer, the term of this patent is extended or adjusted under 35 U.S.C. 154(b) by 1862 days.

(21) Appl. No.: 11/190,723

(22) Filed: Jul. 27, 2005

Related U.S. Application Data

(60) Provisional application No. 60/591,494, filed on Jul. 27, 2004.

(51) Int. Cl.
A61B 5/02 (2006.01)
(52) U.S. Cl. ............................. 600/508; 2/463
(58) Field of Classification Search .................. 607/2, 9; 2/2.5, 463; 600/508, 520; 601/41
See application file for complete search history.

(56) References Cited

U.S. PATENT DOCUMENTS

| 4,441,211 | A | 4/1984 | Donzis |
| 4,535,478 | A | 8/1985 | Zufle |
| 5,495,620 | A | 3/1996 | Schoenweiss et al. |
| 5,621,914 | A | 4/1997 | Ramone et al. |
| 5,742,947 | A | 4/1998 | Davis |
| 5,950,249 | A | 9/1999 | Clement |
| 6,035,452 | A | 3/2000 | Braxton |
| 6,295,654 | B1 | 10/2001 | Farrell |
| 6,446,273 | B1 | 9/2002 | Gillen et al. |
| 6,521,914 | B2 | 2/2003 | Krames et al. |
| 7,503,080 | B2 | 3/2009 | Link |
| 2006/0080762 | A1 * | 4/2006 | Kobren et al. ..................... 2/463 |

FOREIGN PATENT DOCUMENTS

| JP | 1-65073 | 4/1989 |
| WO | WO-2006092551 A1 | 9/2006 |

OTHER PUBLICATIONS

M.S Link. Porgress in Biophysics and Molecular Biology 82 (2003) 175-186.*
Abrunzo *Am. J. Dis. Child.*, 145(11):1279-1282 (1991).
Alder et al. Kyle SB, ed. Youth Baseball Protective Equipment Project Final Report, Washington, D.C., United States Consumer Product Safety Commission, pp. 1-43 (1996).
Chen et al. *Circ. Res.*, 62(6):1191-1209 (1988).
Chou et al. *Electrocardiography in Clinical Practice*, Philadelphia, W. B. Saunders, Chapter 31, pp. 649-655 (1996).
Cooper et al. *J. Trauma*, 22(12):994-1008 (1982).
Deady et al. *J. Emerg. Med.*, 17(3):459-462 (1999).
Dickman et al. *Phys. Sport Med.*, 6:85-86 (1978).

(Continued)

*Primary Examiner* — Carl H Layno
*Assistant Examiner* — Brian T Gedeon
(74) *Attorney, Agent, or Firm* — Mintz Levin Cohn Ferris Glovsky and Popeo, P.C.

(57) ABSTRACT

A method of evaluating a chest wall protector comprises determining a flight time to impact on a subject of a projectile launched using a bow, determining an actuation time of a mechanism configured to release a string of the bow to launch the projectile based upon a desired time of receipt of energy from the projectile by a heart of the subject, determining an external location on an exterior surface of the subject corresponding to where a left ventricle of the heart of the subject is desirably close to the external surface, arranging at least one of the subject and the bow such that a flight path of the projectile is directed at the determined external location, disposing a protector device in the projectile's flight path in contact with the subject, actuating the mechanism at the actuation time, and monitoring a heartbeat of the subject before and after transfer of energy from the projectile to the subject.

7 Claims, 4 Drawing Sheets

OTHER PUBLICATIONS

Estes et al. *Am J. Cardiol.*, 91(Suppl.):45D-52D (2003).
Franz et al. *Circulation*, 86(3):968-978 (1992).
Franz *Cardiac Electrophysiology: From Cell to Bedside*, Zipes, Jalife eds., Second Edition, Philadelphia, W.B. Saunders Company, Chapter 57, pp. 597-606 (1995).
Garan et al. *J. Cardiovasc. Electrophysiol.*, 16(4):433-438 (2005).
Higgins et al. *J. Am. Coll. Cardiol.*, 36(3):824-827 (2000).
Hou et al. *Circulation*, 92(9):2558-2564 (1995).
Howe et al. *Acta Anat.*, 71(1):13-21 (1968).
Kaplan et al. *J. Trauma*, 34(1):151-153 (1993).
Kohl et al. *Prog. Biophys. Mol. Biol.*, 71:91-138 (1999).
Liedtke et al. *Am J. Physiol.*, 226(2):377-382 (1974).
Link et al. *J. Cardiovasc. Electrophysiol.*, 7(7):653-670 (1996).
Link et al. *Commotio Cordis*, in "Sudden Cardiac Death in the Athlete", Futura, Armonk, NY, Chapter 29, pp. 515-528 (1997).
Link et al. *Chest*, 114:326-328 (1998).
Link et al. *N. Engl. J. Med.*, 338(25):1805-1811 (1998).
Link et al. *Circulation*, 98:I-51, abstract 254 (1998).
Link et al. *J. Am. Coll. Cardiol.*, 31(2-Suppl. A):403A, abstract 910-2 (1998).
Link et al. *Cardiol. Review*, 7(5):265-269 (1999).
Link et al. *J. Am. Coll. Cardiol.*, 33(2-Suppl. A):534A, abstract 1210-161 (1999).
Link et al. *J. Am. Coll. Cardiol.*, 33(2-Suppl. A):405A, abstract 1026-82 (1999).
Link et al. *Circulation*, 100(18):I-873-I-864, abstract 4612 (1999).
Link et al. *Ciculation*, 100:413-418 (1999).
Link *Heart*, 81:109-110 (1999).
Link et al. *Exercise and Sports Cardiology*, "Sudden Death and Other Cardiovascular Manifestations of Chest Wall Trauma in Sports", N.Y., McGraw-Hill, Chapter 12, pp. 249-263 (2000).
Link et al. *J. Am. Coll. Cardiol.*, 35(2-Suppl. A):161A, abstract 910-6 (2000).
Link et al. *J. Am. Coll. Cardiol.*, 37(2-Suppl. A):135A, abstract 1297-113 (2001).
Link et al. *J. Am. Coll. Cardiol.*, 37(2):649-654 (2001).
Link et al. *PACE*, abstract only, 24:614 (2001).
Link et al. *Pediatrics*, 109(5):873-877 (2002).
Link et al. *J. Cardiovasc. Electrophysiol.*, 14:83-87 (2003).
Link et al. *J. Am. Coll. Cardiol.*, 41(1):99-104 (2003).
Link, M.S. *Progress Biophys. Mol. Biol.*, 82:175-186 (2003).
Link et al. *Diagnosis and Management of Hypertrophic Cardiomyopathy*, "Sudden Death Due to Chest Blows (Commotio Cordis)", Chapter 29, pp. 432-447 (2004).
Link et al. *Cardiac Mechano-Electric Feedback and Arrhythmias from Pipette to Patient*, Chapter 15, pp. 137-144 (2005).
Link et al. *Cardiac Mechano-Electric Feedback and Arrhythmias from Pipette to Patient*, Chapter 29, pp. 270-276 (2005).
Link et al. *Italian Geart J.*, 6(4):281-283 (2005).
Maron et al. *N. Engl. J. Med.*, 333(6):337-342 (1995).
Maron et al. *Am. J. Cardiol.*, 79:840-841 (1997).
Maron et al. *J. Caardiovasc. Electrophysiol.*, 10:114-120 (1999).
Maron et al. *Circulation*, 102(18):II-609, abstract 2953 (2000).
Maron et al. *JAMA*, 287:1142-1146 (2002).
Maron et al. *JACC*, 45(8):1371-1373 (2005).
Mead et al. *J. Appl. Physiol.*, 5:779-796 (1953).
Mittman et al. *J. Appl. Physiol.*, 20(4):1211-1216 (1965).
Morikawa et al. *Clin. Cardiol.*, 19:831-833 (1996).
Papastamelos et al. *J. Appl. Physiol.*, 78(1):179-184 (1995).
Rashba et al. *Management of Cardiac Arrhythmias*, Humana Press, Totowa, N. J., Chapter 18, pp. 379-418 (2002).
Schnirring *Phys. Sport Med.*, 27(9):19-23 (1999).
Sharp et al. *J. Appl. Physiol.*, 29(6):775-779 (1970).
Viano et al. *Clin. J. Sport Med.*, 2(3):166-171 (1992).
Weinstock et al. *Pediatrics*, 117(4):e1-e7 (2006).
Zabel et al. *Cardiovasc. Res.*, 32(1):120-130 (1996).

* cited by examiner

COMMOTIO CORDIS TESTING

RELATED APPLICATIONS

This application claims priority to U.S. Provisional Application Ser. No. 60/591,494, filed Jul. 27, 2004 and entitled, "Commotio Cordis Testing," and to U.S. application Ser. No. 11/127,548, filed May 12, 2005 and entitled, "Chest Wall Protector," each of which is herein incorporated by reference.

BACKGROUND OF THE INVENTION

Sudden (and usually immediate) death due to impact to the chest (a phenomenon known as commotio cordis) in the absence of underlying cardiac disease has occurred in at least 170 documented cases. The object that initiates commotio cordis generally travels at a speed greater than 25 miles per hour when it strikes the person, which initiates instantaneous ventricular fibrillation. The deaths typically result from impact during sports, e.g., by being hit by a baseball, a puck, a softball, a lacrosse ball, or a hand, foot, or elbow (e.g., in martial arts). Efforts have been undertaken to mandate the use of chest protection for at-risk sports participants, such as baseball and lacrosse players. Assessing the effectiveness of chest wall protection necessitates the development of a model of commotion cordis to understand the mechanism and to evaluate preventive measures.

SUMMARY OF THE INVENTION

Embodiments of the invention are directed to a method of evaluating a chest wall protector. The method includes determining a flight time to impact on a subject of a projectile launched using a bow, determining an actuation time of a mechanism configured to release a string of the bow to launch the projectile based upon a desired time of receipt of energy from the projectile by a heart of the subject, determining an external location on an exterior surface of the subject corresponding to where a left ventricle of the heart of the subject is desirably close to the external surface, arranging at least one of the subject and the bow such that a flight path of the projectile is directed at the determined external location, disposing a protector device in the projectile's flight path in contact with the subject, actuating the mechanism at the actuation time, and monitoring a heartbeat of the subject before and after transfer of energy from the projectile to the subject.

Implementations of the invention may include one or more of the following features. The method may include determining whether commotio cordis is induced in the subject due to the transfer of energy from the projectile to the subject. The actuation time can be a time relative to a reference point of a heartbeat cycle of the subject. The protector can be disposed in direct contact with the subject. The arranging can include using reference markings on a frame of the bow and sighting down the flight path of the projectile to aim the bow.

Further embodiments of the invention are directed to a system for evaluating a chest wall protector's effectiveness for inhibiting commotio cordis due to impact from a projectile. The system includes a launch mechanism configured to couple to the projectile and to launch the projectile toward a subject, the launch mechanism including a bow including a string, and a release mechanism configured to selectively retain the string with the bow in a drawn position, a retaining device configured to hold the subject in a desired position such that the subject can be held in a desired relationship relative to a flight path of the projectile, a monitor configured to monitor a heartbeat of the subject, and a controller coupled to the monitor and to the release and configured to actuate the release to release the string at a desired time relative to a heartbeat cycle of the subject.

Implementations of the invention may include one or more of the following features. The controller can be configured to determine a flight time to impact of the projectile from a test launch and to use the flight time, a period of the heartbeat cycle, a known delay of the release mechanism, and a desired time of energy transfer from the projectile to the heart to determine an actuation time for the release mechanism relative to the heartbeat cycle.

Various aspects of the invention may provide one or more of the following capabilities. Commotio cordis testing can be performed in a highly-repeatable manner. Timing, speed, and/or location of projectile impact for commotio cordis testing can be reproduced consistently. Projectile velocity can be adjusted. Timing of impact of a projectile against a subject relative to the subject's cardiac cycle can be adjusted and selected with a high degree of precision.

These and other capabilities of the invention, along with the invention itself, will be more fully understood after a review of the following figures, detailed description, and claims.

DETAILED DESCRIPTION OF PREFERRED EMBODIMENTS

Embodiments of the invention provide techniques for evaluating apparatus for guarding against commotio cordis. A test system is capable of precise control of speed, timing, and/or location of impact of a projectile upon a test subject. A bow is used to launch a rod with a projectile disposed on a leading end of the rod, with the projectile being or simulating an object of interest such as a sports ball, puck, etc. The bow is released using an electro-mechanical release device controlled by a controller that causes the bow's release to induce impact of the projectile with the subject at a desired time during the subject's heartbeat cycle. The projectile is test fired against the subject to determine timing of release and impact for each subject, and to determine proper sighting of the projectile. The subject is positioned relative to the bow such that the angle of impact of the projectile relative to the subject's chest is about 90°. Other embodiments are within the scope of the invention.

Figure 1:
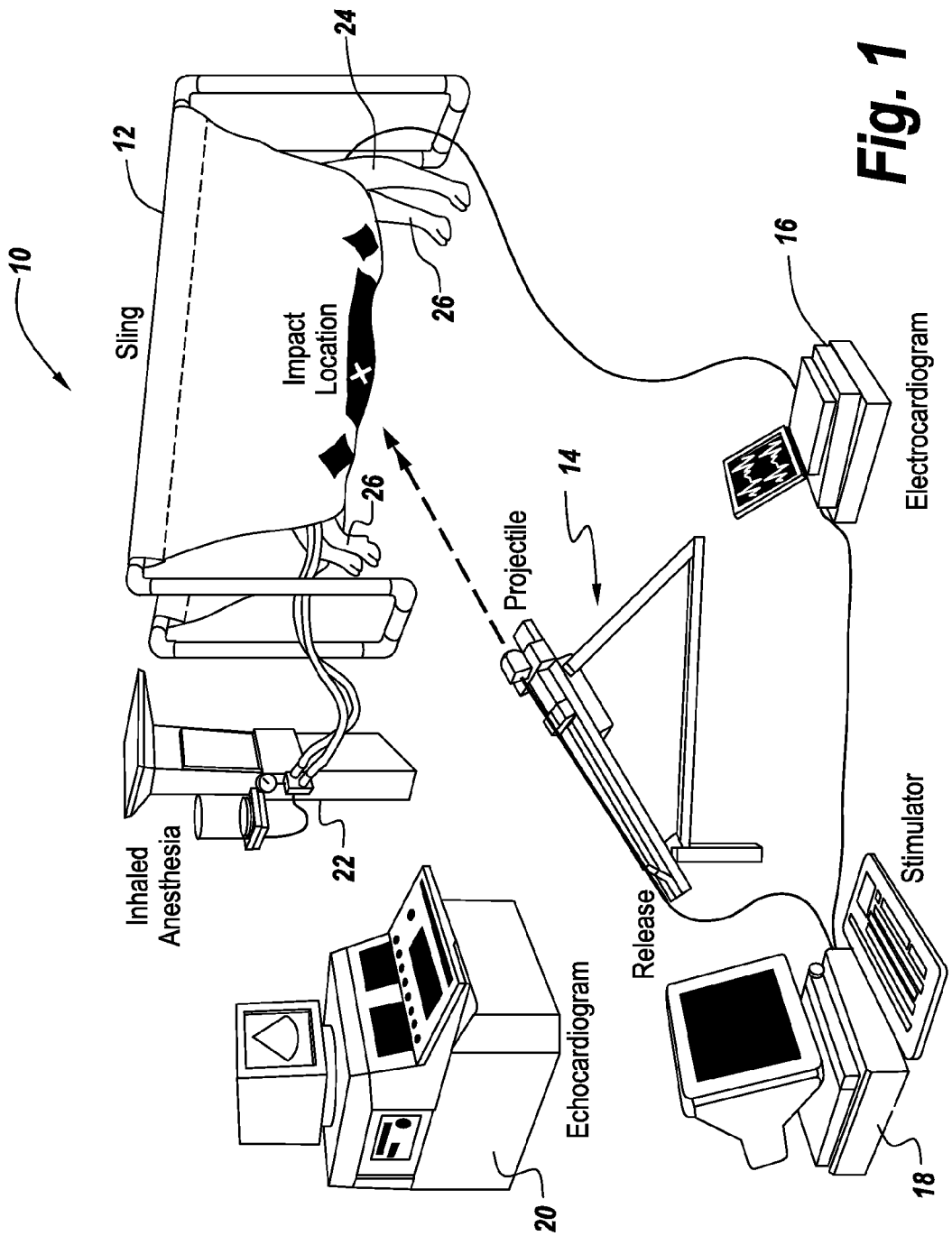
FIG. 1 is a simplified perspective view of a commotio cordis test system.

Referring to FIG. 1, a commotio cordis testing system 10 includes a sling 12, a launch mechanism 14, an electrocardiographic recorder 16, a stimulator 18, an echocardiogram 20, and an anesthesia supply apparatus 22. The sling 12 is configured to hold a test subject 24, here a pig with its legs 26 dangling from either end of the sling 12. The system 10 is configured to control the angle, location, timing, and speed of impact of a projectile into the subject 24 held in the sling 12, and to measure effects of the impact on the subject's heartbeat.

Figure 2:
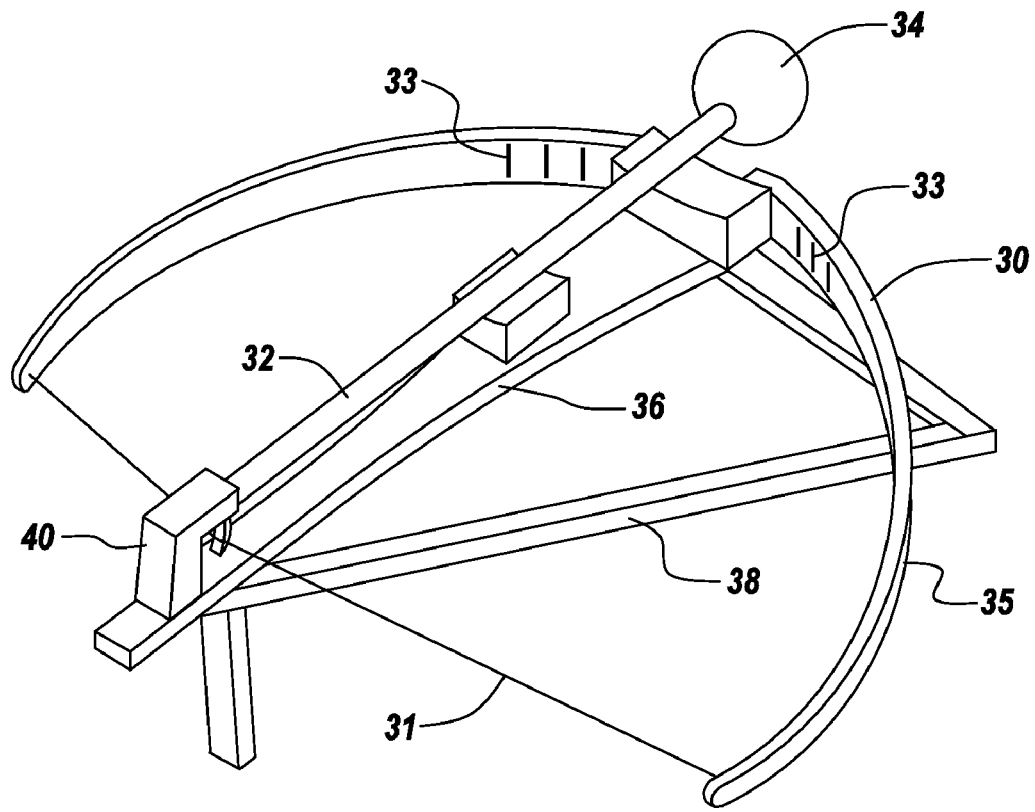
FIG. 2 is a perspective view of a projectile launch mechanism shown in FIG. 1.

Referring also to FIG. 2, the launch mechanism 14 includes a bow 30 (not shown in FIG. 1), a rod 32, a projectile 34, a platform 36, a support frame 38, and a release mechanism 40. The bow 30 is preferably a standard compound hunting bow. It has been found that using a bow provides for better, more repeatable testing than other devices, e.g., a pneumatic launcher, a baseball pitching machine (using one or more rotating wheels), etc. The bow 30 includes a frame 35. The projectile 34 is the object of interest, for example, a baseball, lacrosse ball or hockey puck, or other object that may hit a person. The projectile 34 is attached to the rod 32, such as an aluminum rod. The platform 36 supports and guides the rod 32 and the projectile 34 to hold the projectile 34 and the rod 32 before release of the bow 30 and to direct the projectile 34 to a desired portion of the subject 24. The release mechanism 40 is preferably an electromechanical release under the control of the stimulator 18 that will release a string 31 of the bow 30 to launch the projectile 34 upon receiving a release command from the stimulator 18. The release 40 is stationary such that the bow's string 31 can be pulled to substantially the same location for each use and the force on the string 31 of the bow 30 due to the release mechanism 40 holding the string is repeatable. The release 40 can hold the string 31 with the bow 30 in a drawn position and release the string 31 in response to being actuated to impel the rod 32 and the projectile 34 toward the subject 24. The force applied to the rod 32 and the projectile 34 is thus repeatable, and thus the speed at which the projectile 34 hits the subject 24 is repeatable. The speed may be adjusted by altering the amount that the string 31 is pulled and by adjustment of the draw weight of the bow 30. The stimulator 18 is configured to process data, e.g., by a processor executing stored software instructions, to perform operations as discussed below.

Figure 3:
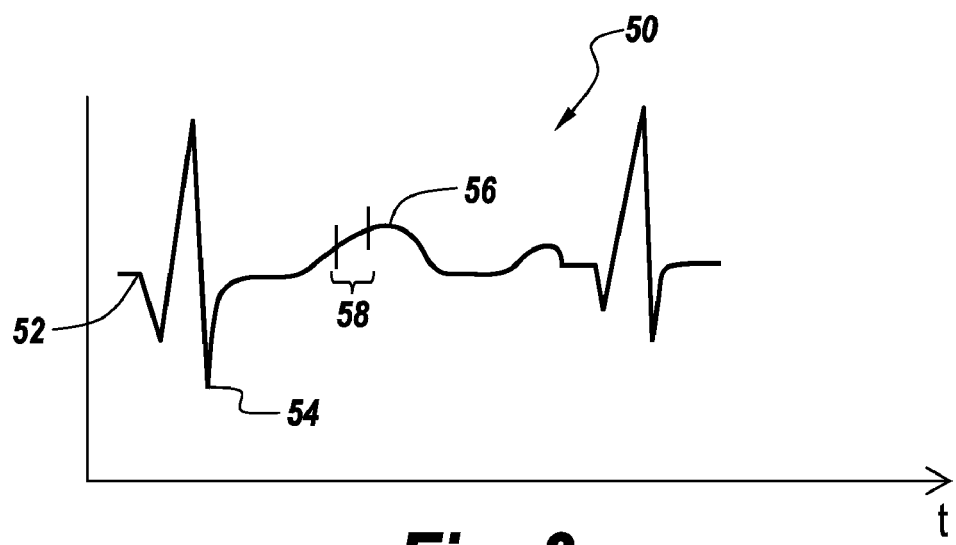
FIG. 3 is a plot of an electrocardiogram output of a heartbeat from a subject shown in FIG. 1.

The electrocardiogram is configured to monitor the heartbeat of the subject 24 and the stimulator 18 is configured to trigger the launcher 14 based upon the subject's heartbeat and a desired timing of impact of the projectile 34 relative to the subject's cardiac cycle. The electrocardiographic recorder 16 can monitor electric signals from the subject's heart and provide R-wave data to the stimulator 18. Referring also to FIG. 3, a plot 50 shows that approximately 60 ms passes from a beginning QRS 52 of a beat, to a trough 54. A peak 56 of the T-wave is approximately 300 to 350 ms after the onset of the QRS 52. It has been found that a window 58 from about 30 ms to about 15 ms before the peak 56 of the T-wave is a period of particular vulnerability for chest impact inducing commotio cordis. The release 40 has a solenoid delay of about 5 ms from receipt of actuation signal to release of the bow's string. The launch mechanism 14 is positioned relative to the subject 24 such that the flight time of the projectile 34 from release to impact is of a length such that if the release 40 is actuated at the beat beginning 52, the projectile 34 will hit the subject 24 during the window 58 of the T-wave. The stimulator 18 marks each QRS 52 and puts out an electrical stimulus to the release 40 which causes release of the rod 32. The time interval from the QRS 52 to the output electrical stimulus is adjustable in 1 ms time intervals. The flight time of the rod 32 and projectile 34 is between 150 and 400 ms, depending on the velocity. The flight time is determined by a test shot in which the projectile 34 is released toward a leg of the subject 24.

Figure 4:
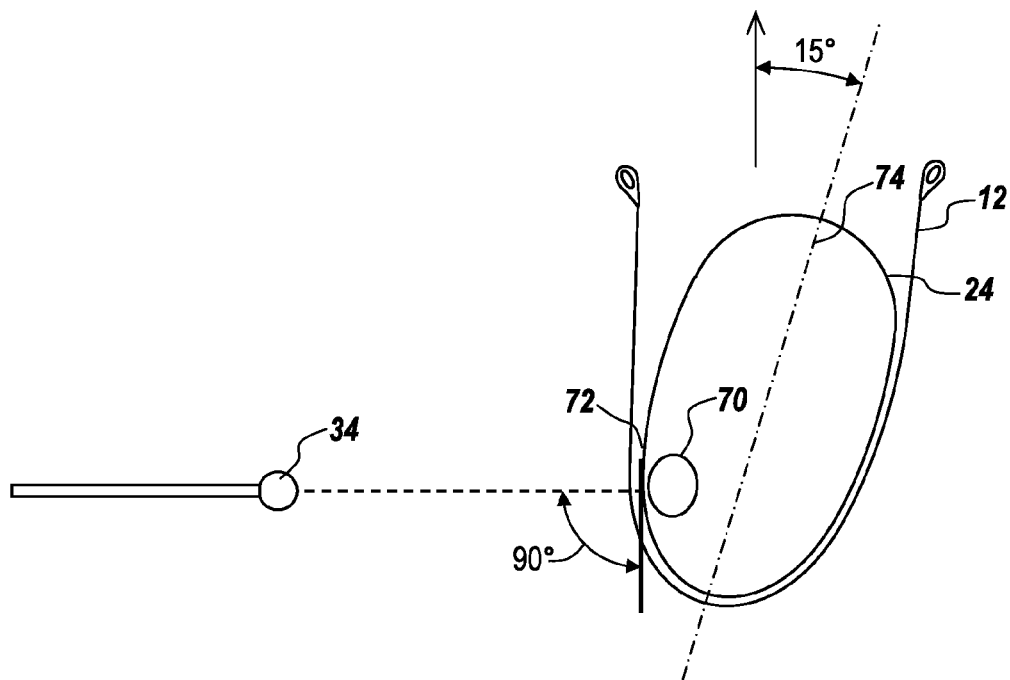
FIGS. 4-5 are side views of portions of the system shown in FIG. 1 including the projectile launch mechanism also shown in FIG. 2 and a cross-sectional view of a test subject and a subject-positioning sling shown in FIG. 1 along a plane transverse to a sagital plane, with and without a chest protector between the subject and the sling.
Figure 5:
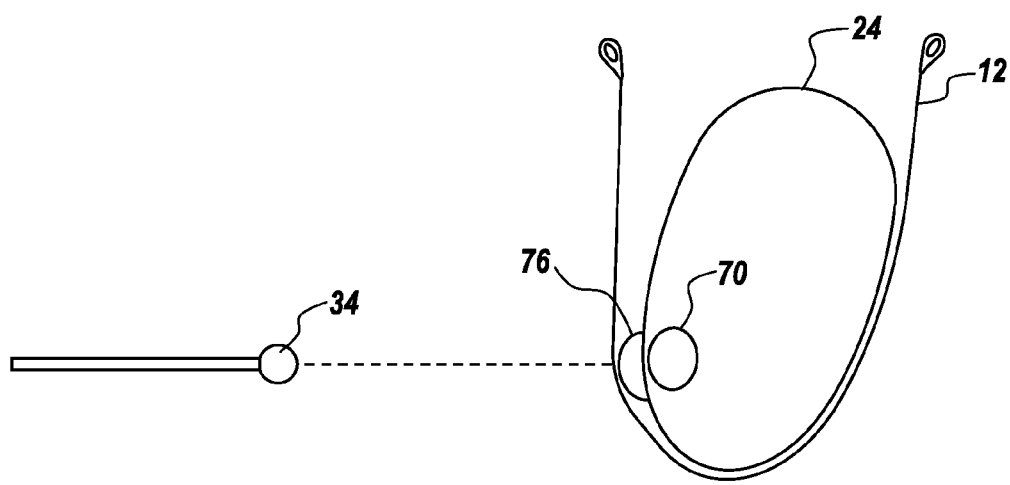

Referring to FIGS. 4-5, with further reference to FIGS. 1-2, the subject 24 is arranged, and the launcher 14 is set up, such that the projectile 34 is directed at substantially the center of the heart 70 of the subject 24. Only the rod 32 and the projectile 34 of the launcher 14 are shown in FIGS. 4-5 for simplicity. The subject 24 and the launcher 14 are arranged such that the projectile 34 will be directed at about a 90° angle relative to the chest wall 72 of the subject 24 and hit the chest wall 72 where the distance from the chest wall 72 to the left ventricle is at or near its minimum. The echocardiogram 20 is used to probe the subject 24 to determine where the left ventricle is closest to the chest wall 72. While this location varies from subject to subject, for a pig this location typically means that the angle of impact of the projectile 34 is at about a 15° upward angle relative to horizontal. Thus, as shown, the launch mechanism 14 is set up to fire the projectile 34 horizontally and the subject is tilted approximately 15° away from the launcher 34 relative to a standing, upright position (relative to the sagital plane 74). In FIG. 5, a chest wall protector 76 is inserted between the chest wall 72 and the sling 12 between the projectile 34 and the heart 70. Adjustments in the release time of the projectile 34 to account for the depth of the protector 76 may be made such that the force transferred to the subject 24 from the projectile 34 reaches the heart 70 at a desired time, e.g., in the known critical window for inducing commotio cordis. Using this setup, and by firing the projectile 34 such that the heart 70 receives the force of the projectile's impact in the known critical time window, the ability and/or effectiveness of the heart/chest wall protector 76 in inhibiting commotio cordis may be evaluated. Further, results using this setup, with the protector 76, and with a setup without the protector 76 can be compared to evaluate the effectiveness of the protector 76 in inhibiting commotio cordis or other effects of the projectile's impact.

Figure 6:
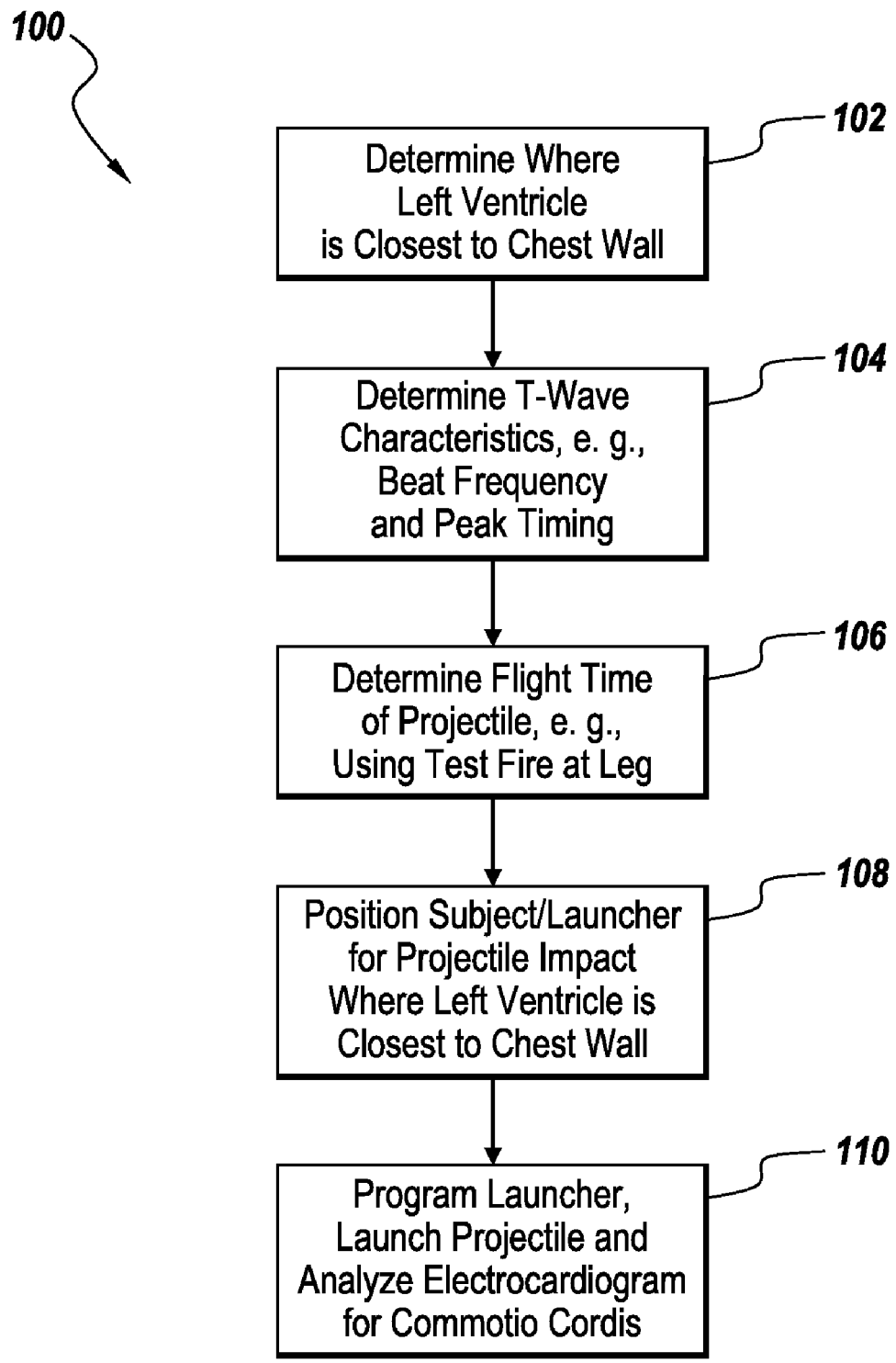
FIG. 6 is a block flow diagram of a process of testing for commotio cordis in the subject shown in FIG. 1.

In operation, referring to FIG. 6, with further reference to FIGS. 1-5, a process 100 for testing chest wall protectors using the system 10 includes the stages shown. The process 100, however, is exemplary only and not limiting. The process 100 may be altered, e.g., by having stages added, removed, or rearranged.

At stage 102, the location of the subject 24 where substantially the center of the heart 70 is closest to the chest wall 72 is determined. The user of the system 10 operates the echocardiogram 20 to take measurements, and evaluates the measured data to determine the point where the heart 70 is closest to the wall 72.

At stage 104, the QRS and T-wave characteristics of the subject's heart 70 are determined. The user operates the electrocardiographic recorder 16 to measure the time from onset of the QRS 52 to the peak 56 of the T-wave. The time to vulnerable period 58 is determined by taking the time in ms from the QRS 52 to the peak of the T-wave 56 and subtracting 15 to 30 ms. Other characteristics may also be determined.

At stage 106, the flight time of the projectile 34 is determined. The subject 24 is positioned with a point of impact on the subject's leg being at the same distance from the projectile 34 as the point of impact will be for impact at the subject's heart 70. The projectile is test fired/launched and the T-wave electrocardiogram monitored for disturbance. The flight time of the projectile 34 is determined by measurement on the electrocardiographic recorder 16 by determining the time from release to impact based on the monitored electrocardiogram disturbance.

At stage 108, the subject 24 and/or the launcher 14 is(are) positioned to provide for a desired impact of the projectile 34 against the subject 24. The flight path and/or point of impact of the projectile 34 is determined by sighting down the launch mechanism 14 from a proximal portion (e.g., the release 32) toward the subject 24. The subject 24 and launcher 14 are arranged with respect to each other such that the flight time will be substantially the same as for the test launch, and such that the projectile's flight path is directed at the spot on the chest wall 72 closest to the left ventricle of the heart 70 and at an angle approximately perpendicular to the chest wall 72 at that point. For a pig, and with the rod 32 substantially horizontal before release, this orientation typically means tilting the subject 24 about 15° from a standing orientation of the subject 24, exposing the underside of the subject 24 slightly to the launcher 14. If a protector is being evaluated, the protector 76 is preferably placed in the flight path of the projectile 34 covering the location of the chest wall 72 closest to the left ventricle of the heart 70. Preferably, the protector 76 is disposed in direct contact with the subject 24 as shown, although the protector 76 could be disposed in indirect contact with the subject 24, e.g., externally to the sling 12, with the sling 12 between the protector 76 and the subject 24.

At stage 110, the launcher 14 is programmed and actuated, and results of projectile impact analyzed. The flight time is subtracted from the time to the vulnerable window 58 (in msec) and this is the time that the stimulator 18 triggers the release 40. Thus the time from QRS 52 to the impact is the addition of the time from QRS 52 to release and the flight time, allowing for the vulnerable time window 58 to be struck. The stimulator 18 detects the beginning 52 of a cycle, and actuates the release at the determined actuation time. The launcher 14 launches the projectile 34, that hits the subject 24 and transfers energy to the subject 24 and the protector 76. The electrocardiographic recorder 16 records the electrocardiogram measurement. The data is analyzed to determine whether commotio cordis was induced and to assess whether the impact occurred during the vulnerable window 58. The process 100 may be repeated with the protector 76, and with different protectors, and the effectiveness of the protector(s) evaluated. The process 100 is preferably repeated without using the protector 76 to determine the effect of the projectile's impact on an unprotected subject. Results of protected and unprotected impacts are analyzed/compared at stage 110 to determine the effectiveness of the protector 76.

In embodiments of the invention, the stimulator 18 can use information from a test firing of the projectile 34 to determine the flight time to the subject 24. The stimulator 18 can use the flight time information and input data as to a desired time of impact relative to the T-wave cycle to determine an actuation time for the release 40 relative to the beginning 52 of a QRS cycle. The stimulator 18 can be configured to receive information about the T-wave from the electrocardiographic recorder 16 and determine the beat frequency by determining the average time between beginnings 52 of beats. The stimulator 18 can also be configured to determine the timing of the peak 56 of the T-wave relative to the T-wave cycle, and thus the window 58 of commotio cordis vulnerability (from about 30 ms before the peak 56 to about 15 ms before the peak 56).

Other embodiments are within the scope and spirit of the appended claims. For example, due to the nature of software, functions described above can be implemented using software, hardware, firmware, hardwiring, or combinations of any of these. Features implementing functions may also be physically located at various positions, including being distributed such that portions of functions are implemented at different physical locations.

What is claimed is:

1. A method of evaluating a chest wall protector, the method comprising:
   determining a flight time to impact on a subject of a projectile launched using a bow;
   determining an actuation time of a mechanism configured to release a string of the bow to launch the projectile based upon a desired time of receipt of energy from the projectile by a heart of the subject;
   determining an external location on an exterior surface of the subject corresponding to where a left ventricle of the heart of the subject is desirably close to the external surface;
   arranging at least one of the subject and the bow such that a flight path of the projectile is directed at the determined external location;
   disposing a protector device in the projectile's flight path in contact with the subject;
   actuating the mechanism at the actuation time; and
   monitoring a heartbeat of the subject before and after transfer of energy from the projectile to the subject.

2. The method of claim 1 further comprising determining whether commotio cordis is induced in the subject due to the transfer of energy from the projectile to the subject.

3. The method of claim 1 wherein the actuation time is a time relative to a reference point of a heartbeat cycle of the subject.

4. The method of claim 1 wherein the protector is disposed in direct contact with the subject.

5. The method of claim 1 wherein the arranging includes sighting down the flight path of the projectile to aim the bow.

6. A system for evaluating a chest wall protector's effectiveness for inhibiting commotio cordis due to impact from a projectile, the system comprising:
   a launch mechanism configured to couple to the projectile and to launch the projectile toward a subject, the launch mechanism including:
      a bow including a string; and
      a release mechanism configured to selectively retain the string with the bow in a drawn position;
   a retaining device configured to hold the subject in a desired position such that the subject can be held in a desired relationship relative to a flight path of the projectile;
   a monitor configured to monitor a heartbeat of the subject; and
   a controller coupled to the monitor and to the release and configured to actuate the release to release the string at a desired time relative to a heartbeat cycle of the subject.

7. The system of claim 6 wherein the controller is configured to determine a flight time to impact of the projectile from a test launch and to use the flight time, a period of the heartbeat cycle, a known delay of the release mechanism, and a desired time of energy transfer from the projectile to the heart to determine an actuation time for the release mechanism relative to the heartbeat cycle.

* * * * *